United States Patent
Singh et al.

(10) Patent No.: US 11,980,792 B2
(45) Date of Patent: May 14, 2024

(54) METHOD AND APPARATUS FOR CALIBRATING A USER ACTIVITY MODEL USED BY A MOBILE DEVICE

(71) Applicant: Qeexo, Co., San Jose, CA (US)

(72) Inventors: Karanpreet Singh, Blacksburg, VA (US); Rajen Bhatt, McDonald, PA (US)

(73) Assignee: QEEXO, CO., San Jose, CA (US)

( * ) Notice: Subject to any disclaimer, the term of this patent is extended or adjusted under 35 U.S.C. 154(b) by 653 days.

(21) Appl. No.: 16/582,241

(22) Filed: Sep. 25, 2019

(65) Prior Publication Data

US 2020/0384313 A1    Dec. 10, 2020

Related U.S. Application Data

(60) Provisional application No. 62/857,330, filed on Jun. 5, 2019.

(51) Int. Cl.
*G16H 20/30*    (2018.01)
*A63B 24/00*    (2006.01)
(Continued)

(52) U.S. Cl.
CPC ...... *A63B 24/0062* (2013.01); *A63B 24/0087* (2013.01); *G06V 40/23* (2022.01);
(Continued)

(58) Field of Classification Search
CPC ............ A23B 24/0062; A63B 24/0087; A63B 2024/0065; A63B 2024/0068;
(Continued)

(56) References Cited

U.S. PATENT DOCUMENTS 9,013,452 B2   4/2015   Harrison
9,019,244 B2   4/2015   Harrison
(Continued)

FOREIGN PATENT DOCUMENTS

CN   107818339 A   * 3/2018
EP     2280337 A2    2/2011
(Continued)

OTHER PUBLICATIONS

Singh, et al. "Personalizing Smartwatch Based Activity Recognition Using Transfer Learning." https://arxiv.org/abs/1909.01202v1, Sep. 3, 2019, 6 pages.
(Continued)

*Primary Examiner* — Catherine T. Rastovski
*Assistant Examiner* — Yossef Korang-Beheshti
(74) *Attorney, Agent, or Firm* — XSENSUS LLP

(57) ABSTRACT

Systems, computer-implemented methods, and computer program products that can facilitate calibrating a user activity model of a user device nodes are described. According to an embodiment, a method for calibrating a user activity model used by a mobile device can comprise receiving sensor data from a sensor of the mobile device. Further, applying a first weight to a first a first likelihood of a first occurrence of a first activity, wherein the first likelihood is determined by a first estimator of the user activity model by applying preconfigured criteria to the sensor data. The method can further comprise performing an action based on a determination of the first occurrence of the first activity, the determination being based on the first weight and the first likelihood of the first occurrence of the first activity.

17 Claims, 14 Drawing Sheets

(51) Int. Cl.
    G06V 40/20       (2022.01)
    H04M 1/72454     (2021.01)
(52) U.S. Cl.
    CPC ............. *G06V 40/25* (2022.01); *G16H 20/30*
        (2018.01); *H04M 1/72454* (2021.01); *A63B
        2024/0065* (2013.01); *A63B 2024/0068*
        (2013.01); *A63B 2024/0071* (2013.01); *A63B
        2220/40* (2013.01); *A63B 2220/52* (2013.01)
(58) Field of Classification Search
    CPC ........ A63B 2024/0071; A63B 2220/40; A63B
            2220/52; G06V 40/23; G06V 40/25;
            H04M 1/72454; A61B 5/1118; A61B
            5/1123; A61B 2560/0223; G16H 50/50
    See application file for complete search history.

(56)                References Cited

U.S. PATENT DOCUMENTS

| | | | |
|---|---|---|---|
| 10,599,250 | B2 | 3/2020 | Harrison |
| 2005/0083313 | A1 | 4/2005 | Hardie-Bick |
| 2008/0036743 | A1 | 2/2008 | Westerman |
| 2009/0231275 | A1 | 9/2009 | Odgers |
| 2010/0251112 | A1 | 9/2010 | Hinckley |
| 2010/0279738 | A1 | 11/2010 | Kim |
| 2011/0018825 | A1 | 1/2011 | Kondo |
| 2011/0057885 | A1 | 3/2011 | Lehtovirta |
| 2012/0019562 | A1 | 1/2012 | Park |
| 2012/0254100 | A1 | 10/2012 | Grokop |
| 2013/0257757 | A1 | 10/2013 | Kim |
| 2013/0316813 | A1 | 11/2013 | Derome |
| 2014/0109004 | A1 | 4/2014 | Sadhvani |
| 2014/0210788 | A1 | 7/2014 | Harrison |
| 2014/0240295 | A1 | 8/2014 | Harrison |
| 2014/0267085 | A1 | 9/2014 | Li |
| 2014/0289659 | A1 | 9/2014 | Harrison |
| 2015/0326709 | A1* | 11/2015 | Pennanen ............. A61B 5/1118 455/456.6 |
| 2016/0007935 | A1 | 1/2016 | Hernandez |
| 2016/0253594 | A1* | 9/2016 | Chowdhary ........... G06N 7/005 706/52 |
| 2018/0204128 | A1* | 7/2018 | Avrahami ............ G06Q 10/109 |
| 2018/0333057 | A1* | 11/2018 | Chowdhary ......... A61B 5/7267 |
| 2019/0183428 | A1* | 6/2019 | Fu ........................ A61B 5/1115 |
| 2020/0250508 | A1* | 8/2020 | De Magalhaes ....... G06N 3/006 |

FOREIGN PATENT DOCUMENTS

| | | | |
|---|---|---|---|
| JP | 2004213312 | A | 7/2004 |
| KR | 20020075283 | A | 10/2002 |
| WO | 2012087308 | | 6/2012 |
| WO | 2013059488 | A1 | 4/2013 |

OTHER PUBLICATIONS

Corrected Notice of Allowance dated Feb. 22, 2021 for U.S. Appl. No. 16/788,940 (pp. 1-5).
International Search Report and Written Opinion for App. No. PCT/US20/35886, dated Aug. 18, 2020, 9 pages.
Notice of Allowance dated Feb. 4, 2021 for U.S. Appl. No. 16/788,940 (pp. 1-8).
U.S. Appl. No. 13/887,711, CTAV—Advisory Action (Ptol-303), dated Oct. 8, 2019, 3 pages.
U.S. Appl. No. 13/887,711, Notice of Allowance and Fees Due (Ptol-85), dated Feb. 3, 2020, 2 pgs.
U.S. Appl. No. 13/887,711, USPTO e-Office Action: Notice of Allowance and Fees Due (Ptol-85), dated Nov. 14, 2019, 7 pgs.
Asano et al., "Real-Time Sound Source Localization and Separation System and Its Application to Automatic Speech Recognition", Proceedings of Eurospeech, 2001; p. 1013-1016; 2001.
Benko et al. "Sphere: Multi-Touch Interactions on a Spherical Display", Proceedings of UIST, 2008; pp. 77-86.
Burges, Christopher, "A Tutorial on Support Vector Machines for Pattern Recognition," Data Mining and Knowledge Discovery, vol. 2, Issue 2, pp. 121-167, Jun. 1998.
Cao et al., "ShapeTouch: Leveraging Contact Shape on Interactive Surfaces", IEEE International Workshop on Horizontal Interactive Human Computer System (TABLETOP), 2008, pp. 139-146.
Deyle et al., "Hambone: A Bio-Acoustic Gesture Interface", Proceedings of ISWC, 2007, pp. 1-8.
Dietz et al., "DiamondTouch: A Multi-User Touch Technology" ACM Symposium on User Interface Software & Technology (UIST), 2001, pp. 219-226.
Dietz et al., DT Controls: Adding Identity to Physical Interfaces, ACM Symposium on User Interface Software & Technology (UIST), 2005, pp. 245-252.
Final Office Action dated Nov. 28, 2014 in U.S. Appl. No. 13/849,698, 21 pages.
Gutwin et al., "Supporting Informal Collaboration in Shared-Workspace Groupware", Journal of Universal Computer Science, vol. 14, No. 9, 2008, pp. 1411-1434.
Hall et al., "The WEKA Data Mining Software: An Update", SIGKDD Explorations, vol. 11, No. 1, 2009, pp. 10-18.
Harrison et al., "Scratch Input: Creating Large, Inexpensive, Unpowered and Mobile Finger Input Surfaces", Proceedings of UIST, 2008, pp. 205-208.
Harrison et al., Skinput: Appropriating the Body as an Input Surface, Proceedings of CHI, Apr. 10-15, 2010, pp. 453-462.
Hartmann et al., "Augmenting Interactive Tables with Mice & Keyboards", Proceedings of UIST, 2009, pp. 149-152.
Hinckley et al., "Pen+ Touch= New Tools", Proceedings of UIST, 2010, pp. 27-36.
Hinckley et al., "Sensor Synaesthesia: Touch in Motion, and Motion in Touch", Proceedings of CHI, 2011, pp. 801-810.
Holz et al., "The Generalized Perceived Input Point Model and How to Double Touch Accuracy by Extracting Fingerprints" Proceedings of CHI, 2010, pp. 581-590.
International Search Report and Written Opinion received for International Patent Application No. PCT/US2012/060865 dated Mar. 29, 2013, 10 pages.
International Search Report and Written Opinion received for PCT Application No. PCT/US2014/034977 dated Sep. 18, 2014, 8 pages.
International Search Report and Written Opinion received for PCT Application No. PCT/US2014/049485 dated Nov. 17, 2014, 13 pages.
Kaltenbrunner, M. et al., "reacTIVision: A Computer-Vision Framework for Table-Based Tangible Interaction," Proceedings of TEI, 2007, pp. 69-74.
Matsushita et al., "HoloWall: Designing a Finger, Hand, Body, and Object Sensitive Wall", Proceedings of UIST, 1997, pp. 209-210.
Non-Final Office Action dated Jun. 24, 2014 in U.S. Appl. No. 13/849,698, 21 pages.
Non-Final Office Action dated Oct. 16, 2014 in U.S. Appl. No. 13/780,494, 10 pages.
Non-Final Office Action received for U.S. Appl. No. 13/958,427, dated Mar. 13, 2015, 50 pages.
Non-Final Office Action—dated Oct. 16, 2014—U.S. Appl. No. 13/780,494, filed Feb. 28, 2013, titled: "Input Tools Having Viobro-Acoustically Distinct Regions and Computing Device for Use With the Same." (12 pages).
Olwal et al., "SurfaceFusion: Unobtrusive Tracking of Everyday Objects in Tangible User Interfaces", Proceedings of GI, 2008, pp. 235-242.
Paradiso et al., "Tracking and Characterizing Knocks Atop Large Interactive Displays", Sensor Review, vol. 25, No. 2, 2005, pp. 134-143.
Paradiso, J. et al., "Sensor Systems for Interactive Surfaces," IBM Systems Journal, vol. 39, Issue 3-4, pp. 892-914, 2000.
Patten, James, Mcmichael., "Sensetable: A Wireless Object Tracking Platform for Tangible User Interfaces", Proceedings of CHI, 2001, pp. 253-260.
Pedro, L et al., "Augmenting touch interaction through acoustic sensing", Proceedings of the ACM International 3onference on Interactive Tabletops and Surfaces, pp. 53-56, Nov. 13-16, 2011.

(56) References Cited

OTHER PUBLICATIONS

Rekimoto et al., "Augmented Surfaces: A Spatially Continuous Work Space for Hybrid Computing Environments", Proceedings of CHI, 1999, pp. 378-385.
Rekimoto et al., "SmartSkin: An Infrastructure for Freehand Manipulation on Interactive Surfaces", Proceedings of CHI, 2002, pp. 113-120.
Rekimoto et al., "ToolStone: Effective use of the Physical Manipulation Vocabularies of Input Devices", Proceedings of UIST, 2000, pp. 109-117.
Stevan Vigneaux, Director of Product Management, Mimio, "Choosing and Installing a Whiteboard for a Touch Projector", www.mimio.boxlight.com, Jan. 15, 2020. 10 pages.
U.S. Appl. No. 14/483,150, filed Sep. 11, 2014, titled: "Method and Apparatus for Differentiating Touch Screen Users Based on Touch Event Analysis."
U.S. Appl. No. 14/492,604, filed Sep. 22, 2014, titled: "Method and Apparatus for Improving Accuracy of Touch Screen Event Analysis by Use of Edge Classification."
U.S. Appl. No. 14/495,041, filed Sep. 24, 2014, titled: "Method for Improving Accuracy of Touch Screen Event Analysis by Use of Spatiotemporal Touch Patterns."
U.S. Appl. No. 14/191,329, filed Feb. 26, 2014, titled "Using Capacitive Images for Touch Type Classification", 42 pages.
U.S. Appl. No. 13/849,698, filed Mar. 25, 2013, titled: "Method and System for Activating Different Interactive Functions Using Different Types of Finger Contacts." 52 pages.
U.S. Appl. No. 13/958,427, filed Aug. 2, 2013, titled: "Capture of Vibro-Acoustic Data Used to Determine Touch Types." 45 pages.
U.S. Appl. No. 14/242,127, filed Apr. 1, 2014, titled: "Method and Apparatus for Classifying Touch Events on a Touch Sensitive Surface.", 36 pages.
U.S. Appl. No. 14/483,150, filed Sep. 11, 2014, titled: "Method and Apparatus for Differentiating Touch Screen Users Based on Touch Event Analysis." 38 pages.
U.S. Appl. No. 14/492,604, filed Sep. 22, 2014, titled: "Method and Apparatus for Improving Accuracy of Touch Screen Event Analysis by Use of Edge Classification." 35 pages.
U.S. Appl. No. 14/495,041, filed Sep. 24, 2014, titled: "Method for Improving Accuracy of Touch Screen Event Analysis by Use of Spatiotemporal Touch Patterns." 34 pages.
Vandoren et al., "DIP-IT: Digital Infrared Painting on an Interactive Table", Proceedings of CHI, 2008, pp. 2901-2906.
Wang et al., "Empirical Evaluation for Finger Input Properties in Multi-Touch Interaction", Proceedings of CHI, 2009, pp. 1063-1072.
Extended European Search Report issued in App. No. EP20817902, dated Jun. 6, 2023, 8 pages.

\* cited by examiner

TUNING OF GBM PARAMETERS

Once a GBM is trained, it is used to predict the output for any particular inputs. Initially, the decision functions from all the estimators is predicted. For example, the decision function, $\phi_{jp}$, is calculated from $j^{th}$ estimator for $p^{th}$ class. Later, a final score is calculated for $p^{th}$ class in a multi-class output as $$f_p = \phi_{0p} + \sum_{j=1}^{n} w_{jp}\phi_{jp}$$

where, $n$ is the total number of estimators, $\phi_{0p}$ is the initial guess for $p^{th}$ class, $\phi_{jp}$ is the decision output from $j^{th}$ estimator for $p^{th}$ class and $w_{jp}$ is the weight attached to this $j^{th}$ estimator.

The score output for the each class is used to find the probability, $P(p)$, of $p^{th}$ class by using softmax function as $$P(p) = \frac{\exp(f_p)}{\sum_{q=1}^{l} \exp(f_q)}$$

where, $l$ is the total number of classes. Finally, an output is predicted to be the class having the maximum probability.

FIG. 3

To train the weights of the GBM, different loss functions can be used. For example, if mean squared error is used as the loss function to train the weights, the loss function can be defined as $$L = \frac{1}{l}\sum_{p=1}^{l}(P(p) - P(p))^2$$

where, $P(p)$ is the ground truth probability for $p^{th}$ class. This probability would be 1 for one of the classes and 0 for the remaining classes for any particular input.

The gradient of the loss function with respect to weight $w_{jp}$ can be defined as $$\frac{\partial L}{\partial w_{jp}} = \frac{2}{l}\sum_{p=1}^{l}(P(p) - P(p))(-\frac{\partial P(p)}{\partial w_{jp}})$$

where, $$\frac{\partial P(p)}{\partial w_{jp}} = P(p)\frac{\partial f_p}{\partial w_{jp}} - (P(p))^2\frac{\partial f_p}{\partial w_{jp}}$$

and $$\frac{\partial f_p}{\partial w_{jp}} = \phi_{jp}$$

The gradient of the loss function can be used to update the weights as follows, $$w_{jp} = w_{jp} - \eta\frac{\partial L}{\partial w_{jp}}$$

FIG. 4

Table 2. Comparison of F1 scores of baseline and tuned GBM across subjects of data set 1

| Subject | Baseline | Tuned GBM | Standard Deviation |
|---|---|---|---|
| #1 | 0.9231 | 0.9549 | 0.0044 |
| #2 | 0.9834 | 0.9904 | 0.0015 |
| #3 | 0.9817 | 0.9842 | 0.0019 |
| #4 | 0.9453 | 0.9917 | 0.0010 |
| #5 | 0.9986 | 0.9997 | 0.0002 |
| #6 | 0.9883 | 0.9935 | 0.0008 |
| #7 | 0.8004 | 0.9440 | 0.0042 |
| #8 | 0.9431 | 0.9685 | 0.0066 |
| Overall | 0.9456 | 0.9784 | 0.0011 |

FIG. 9

Table 3. Comparison of F1 scores of baseline and tuned GBM across subjects of data set II

| Subject | Baseline | Tuned GBM | Standard Deviation |
|---|---|---|---|
| #1 | 0.9231 | 0.9508 | 0.0025 |
| #2 | 0.9612 | 0.9634 | 0.0029 |
| #3 | 0.9368 | 0.9588 | 0.0020 |
| #4 | 0.9551 | 0.9535 | 0.0017 |
| #5 | 0.9468 | 0.9576 | 0.0047 |
| #6 | 0.9759 | 0.9807 | 0.0020 |
| #7 | 0.8117 | 0.9671 | 0.0021 |
| Overall | 0.9307 | 0.9619 | 0.0009 |

FIG. 13

METHOD AND APPARATUS FOR CALIBRATING A USER ACTIVITY MODEL USED BY A MOBILE DEVICE

RELATED APPLICATION

The subject patent application claims priority to U.S. Provisional Patent Application No. 62/857,330 filed Jun. 5, 2019, and entitled "METHOD AND APPARATUS FOR CALIBRATING A USER ACTIVITY MODEL USED BY A MOBILE DEVICE" the entirety of which application is hereby incorporated by reference herein.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

The one or more embodiments relate generally to the field of human computer interaction technology, and more particularly to a method, apparatus and system for calibrating a user activity model used by a mobile device.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Human activity monitoring devices are becoming increasingly popular. Different devices can use different approaches to interpreting data collected from device sensors. Problems can arise however, when models used to interpret sensor data are based on samples from a mainstream group of people.

SUMMARY

The following presents a summary to provide a basic understanding of one or more embodiments of the invention. This summary is not intended to identify key or critical elements or delineate any scope of the particular embodiments or any scope of the claims. Its sole purpose is to present concepts in a simplified form as a prelude to the more detailed description that is presented later. In one or more embodiments described herein, devices, systems, methods, and computer-implemented methods are described that can facilitate calibrating a user activity model of a user device.

According to an embodiment, a method for calibrating a user activity model used by a mobile device can comprise receiving sensor data from a sensor of the mobile device. Further, applying a first weight to a first likelihood of a first occurrence of a first activity, wherein the first likelihood is determined by a first estimator of the user activity model by applying preconfigured criteria to the sensor data. The method can further comprise performing an action based on a determination of the first occurrence of the first activity, the determination being based on the first weight and the first likelihood of the first occurrence of the first activity. In a variation, the first activity can be an activity of a user of the mobile device. The variation can further comprise facilitating an assessment of physical characteristics of the user of the mobile device, and selecting the first weight is based on the assessment of the physical characteristics of the use. In some implementations, wherein the selecting the first weight can comprise selecting the first weight to improve, for the user of the mobile device, an accuracy of the first likelihood of the first occurrence of the first activity. The variation can select the first weight is further based on training data for the first activity. In an additional or alternative embodiment, the determining of the first occurrence of the first activity can comprise comparing the first likelihood of the first occurrence of the first activity to a second likelihood of a second occurrence of a second activity. In the embodiment discussed above, the applying the first weight to the first likelihood can comprise modifying the first likelihood. Further, the receiving the sensor data can comprise, receiving data from at least one of, an accelerometer, a magnetometer, or a gyroscope.

In another embodiment, a mobile device can comprise a sensor, a processor, and a memory that can store executable instructions that, when executed by the processor, facilitate performance of operations including receiving sensor data from the sensor, and applying a first weight to a first likelihood of a first occurrence of a first activity, wherein the first likelihood is determined by a first estimator of the user activity model by applying preconfigured criteria to the sensor data. The operations can further comprise performing an action based on a determination of the first occurrence of the first activity, the determination being based on the first weight and the first likelihood of the first occurrence of the first activity.

In a variation of the embodiment above, the first activity can be activity of a user of the mobile device. Further, the operations can further include facilitating an assessment of physical characteristics of the user of the mobile device, and selecting the first weight is based on the assessment of the physical characteristics of the use. In some embodiments, the selecting the first weight can comprise selecting the first weight to improve, for the user of the mobile device, an accuracy of the first likelihood of the first occurrence of the first activity. In one or more embodiments, the selecting the first weight can be further based on training data for the first activity. Further, the determining of the first occurrence of the first activity can comprise comparing the first likelihood of the first occurrence of the first activity to a second likelihood of a second occurrence of a second activity. In additional or alternative embodiments, the applying the first weight to the first likelihood comprises modifying the first likelihood. In some embodiments, the sensor can comprises one or more of, an accelerometer, a magnetometer, or a gyroscope.

In another embodiment, a computer-readable recording medium having program instructions that can be executed by various computer components to perform operations comprising receiving sensor data from a sensor of a mobile device, and applying a first weight to a first likelihood of a first occurrence of a first activity, wherein the first likelihood is determined by a first estimator of the user activity model by applying preconfigured criteria to the sensor data. In some embodiments, the operations can further include performing an action based on a determination of the first occurrence of the first activity, the determination being based on the first weight and the first likelihood of the first occurrence of the first activity. Further, in this embodiment, the operations can further comprise facilitating an assessment of physical characteristics of a user of the mobile device, and selecting the first weight is based on the assessment of the physical characteristics of the user, wherein the first activity is activity of the user.

In some implementations, the selecting the first weight can comprise selecting the first weight to improve, for the user of the mobile device, an accuracy of the first likelihood of the first occurrence of the first activity. Additionally, in one or more embodiments, the selecting the first weight can be further based on training data for the first activity.

BRIEF DESCRIPTION OF THE DRAWINGS

The included drawings are for illustrative purposes and serve only to provide examples of possible structures and process steps for the disclosed techniques. These drawings in no way limit any changes in form and detail that may be made to embodiments by one skilled in the art without departing from the spirit and scope of the disclosure.

FIG. 3 depicts example formulas that can describe the modifying of a gradient boosting machine (GBM) model parameters, in accordance with one or more embodiments.

FIG. 4 depicts example formulas that can describe using loss functions to select a weight to be applied to an estimator, in accordance with one or more embodiments.

FIGS. 8A-8B, and FIG. 9, continuing this example, respectively depict charts 810-880 and table 900, with accuracy shown before and after the use of generated weights, as described herein.

FIGS. 12 and 13, to illustrate additional aspects of one or more embodiments, respectively depict charts and table showing illustrative data from another example dataset.

DETAILED DESCRIPTION

Applications of methods and apparatus according to one or more embodiments are described in this section. These examples are being provided solely to add context and aid in the understanding of the present disclosure. It will thus be apparent to one skilled in the art that the techniques described herein may be practiced without some or all of these specific details. In other instances, well known process steps have not been described in detail in order to avoid unnecessarily obscuring the present disclosure. Other applications are possible, such that the following examples should not be taken as definitive or limiting either in scope or setting.

In the following detailed description, references are made to the accompanying drawings, which form a part of the description and in which are shown, by way of illustration, specific embodiments. Although these embodiments are described in sufficient detail to enable one skilled in the art to practice the disclosure, it is understood that these examples are not limiting, such that other embodiments may be used and changes may be made without departing from the spirit and scope of the disclosure.

One or more embodiments may be implemented in numerous ways, including as a process, an apparatus, a system, a device, a method, a computer readable medium such as a computer readable storage medium containing computer readable instructions or computer program code, or as a computer program product comprising a computer usable medium having a computer readable program code embodied therein.

The figures in the following description relate to preferred embodiments by way of illustration only. It should be noted that from the following discussion, alternative embodiments of the structures and methods disclosed herein will be readily recognized as viable alternatives that may be employed without departing from the principles of what is claimed.

Generally speaking, one or more embodiments can improve the accuracy of the use of human-computer interaction (HCI) technologies, specifically, HCI interactions where a device selects an activity likely to be occurring based on sensor data of the device. As described further below, one or more embodiments can modify the output of a trained model without retraining the estimators of the model, and in some circumstances described herein, embodiments described herein can significantly increase the accuracy and F-1 scores for the identification of activities for certain types of users and activity classes.

Figure 1:
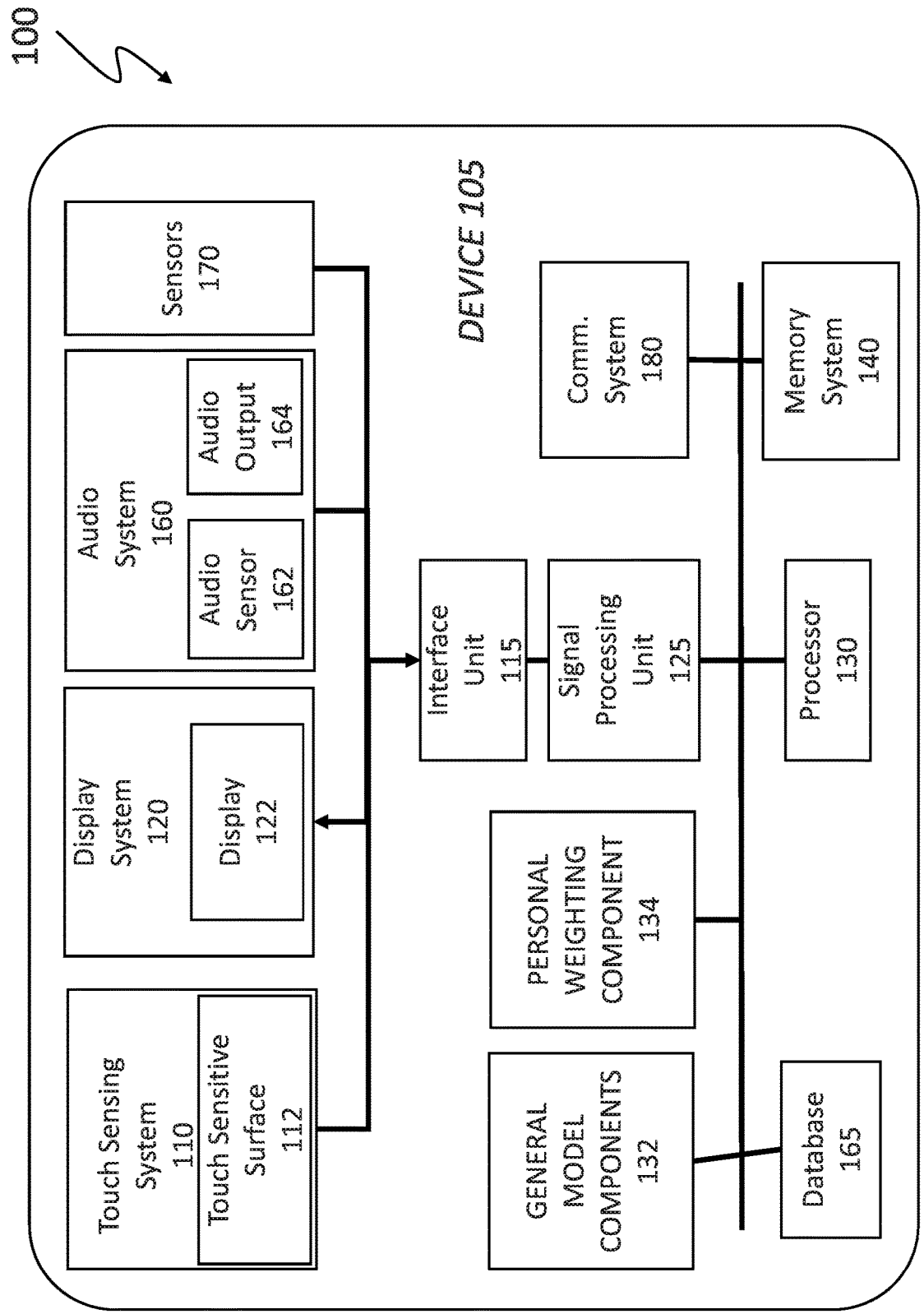
FIG. 1 illustrates an example of a system that can calibrate an activity model used by a device based on weights generated by a personal weight determiner, in accordance with one or more embodiments.

FIG. 1 illustrates an example of a system 100 that can calibrate an activity model used by device 105 based on weights generated by personal weight determiner 175, in accordance with one or more embodiments.

Device 105 can take any of a variety of forms, including but not limited to, a cellular telephone, personal computer, a personal digital assistant, smart watch, and any other device that has sensors 170 capable of sensing different conditions. In this regard, it will be appreciated that while the components of touch sensitive device 105 are illustrated as being within a single housing, this is optional, and these components may be located in separately housed components, such as external sensors configured to provide data to device 105, e.g., a heart rate monitor, pace sensor, step sensor, and other similar sensor components that can be external to the housing of device 105.

Device 105 can include various I/O components, including but not limited to touch sensing system 110, display system 120, audio system 160, and sensors 170, these being coupled in this example via interface unit 115 to signal processing unit 125. Signal processing unit 125 can receive signals from interface unit 115 that can be in digital form, and prepare the signals for further processing. Signal processing unit 125 may perform at least one of sampling, quantization and encoding processes to convert such analog signals into a digital signal. Signal processing unit 125 may provide the digital signals to processor 130 and other system components.

In one or more embodiments, display system 120 can output an image using display 122, touch sensing system 110 can receive touch input using touch sensing surface 112, and audio system output audio using audio sensor 162 (e.g., a microphone and or connection to a microphone) and audio output 164, such as a speaker or connection to a speaker.

Device 105 can also have processor 130 such as a micro-processor, micro-controller, or any other type of programmable control device, or a preprogrammed or dedicated processing or control system. Used by processor 130, device 105 can further include memory system 140. Memory system 140 can be capable of providing programming and other forms of instructions to processor 130 and that can be used for other purposes. Memory system 140 may include read only memory, random access semiconductor memory or other types of memory or computer readable media that may be permanently installed or separably mounted to device 105. Additionally, device 105 can also access another memory system 140 that is separate from touch sensitive device 105 by way of communication system 180. In one or more embodiments, database 165 can also be provided to store programs and other data, e.g., generated personal weights.

Communication system 180 can take the form of any optical, radio frequency or other circuit or system that can convert data into a form that can be conveyed to an external device by way of an optical signal, radio frequency signal or other form of wired or wireless signal. Communication system 180 may be used for a variety of purposes including but not limited to sending and receiving instruction sets and exchanging data with remote sensors or memory systems.

According to one embodiment of the invention, at least some of the functions of general model components 132, personal weight applier 134, personal weight determiner 175, interface unit 115, signal processing unit 125, database 165, and other components discussed below, can be program modules to control or communicate with other commonly known hardware components or components for executing software. In one or more embodiments, program modules can be included in device 105 in the form of operating systems, application program modules or other program modules, and can be physically stored in a variety of commonly known storage devices. Further, the program modules can be stored in a remote storage device that may communicate with touch sensitive device 105 by way of communication system 180. Such program modules can also include, but are not limited to, routines subroutines, programs, objects, components, data structures and the like for performing specific tasks or executing specific abstract data types as described below in accordance with the present invention. Such program modules may also be expressed in terms of configurations of hardware adapted to perform the functions associated with such modules.

To further describe the functions and capabilities of one or more embodiments, general model components 132, personal weight applier 134, and personal weight determiner 175 are discussed with examples below.

Figure 2:
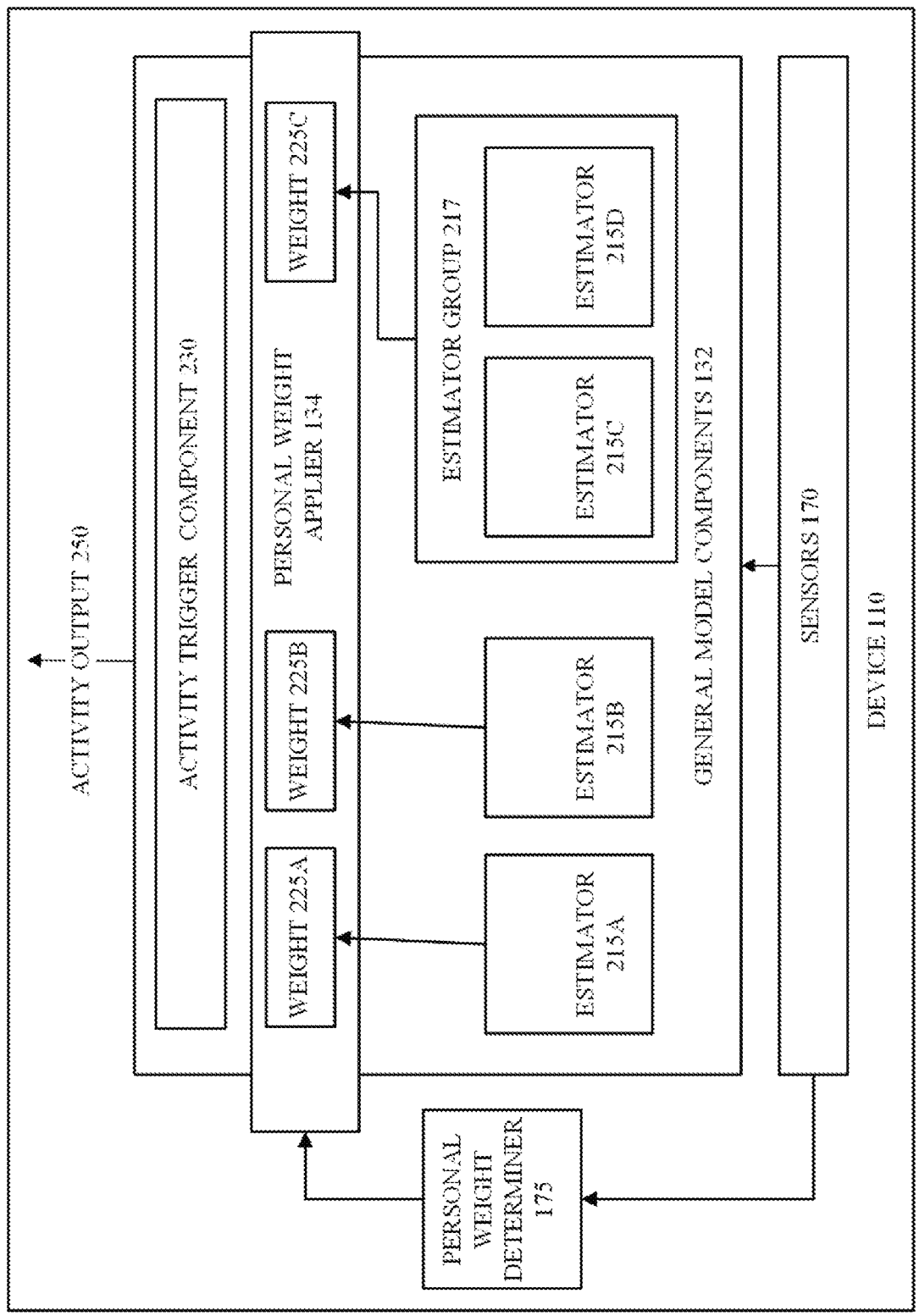
FIG. 2 illustrates a more detailed view of general model components and the operation of a personal weight applier and a personal weight determiner, in accordance with one or more embodiments.

FIG. 2 illustrates a more detailed view of general model components 132 and the operation of personal weight applier 134 and personal weight determiner 175, in accordance with one or more embodiments. Repetitive description of like elements employed in other embodiments described herein is omitted for sake of brevity.

One approach that can be used to recognize activities combines the sensor data with a model that can interpret the data. For example, when a device is in the pocket of a sitting person, example sensor outputs can include the angle of the device as measured by a gyroscope sensor, the stillness of the device measured by an accelerometer, a lack of touches on a touch interface of the device, and other combinations of data, both known and discoverable by experimental use. Based on this example sensor data, a device can determine that the user of the device is likely to be currently sitting, and provide functions based on this determination, e.g., turn off location detecting sensors, provide notifications by a custom vibration, and other actions associated with the determination.

In some implementations, device 105 can determine the occurrence of different activities by employing general model components 132. Included in these components are individual estimators 215A-D that can utilize some or all of analyze sensors 170 data and detect a specific activity or combinations of activities associated with the individual estimators 215A-D. For example, estimator 215A can be configured to determine a likelihood that device 105 is in pocket of a user, e.g., by analyzing light sensor, accelerometer, and gyroscope data. Alternatively, estimator 215A can be configured to identify a combination of activities, e.g., device 105 is in a pocket, and the user is sitting, sensor data associated with this example being discussed with the introduction above. In another alternative, these two activities can be identified by different estimators 215C-D, and, the results can be grouped into an estimator group 217, with a single value being provided for the combination.

In some circumstances, general model components 132, being trained with data designed to accurately measure a majority of users, can be inaccurate for a minority of users. For example, when detecting a "standing up from sitting" activity, the data collected for the standard model may not apply accurately to children, people with disabilities, or elderly people, e.g., the speed and mechanics of the movements of the majority of people can be significantly changed based on youth, disability, or advanced age. Another example activity that can be inaccurately evaluated by standard models, in some circumstances, is a "running" activity. Different users have different concepts of running, with, in some circumstances, the running activity of an elderly person being evaluated as walking, e.g., because of the speed and vigorousness of the movements.

One reasons that the above inaccuracies can occur is that the models used to analyze sensors 170 data to determine likely activities are not customized to the specifics of a particular user. To improve the accuracy of the determination of likely activities by a device, one or more embodiments can receive an indication from a standard model regarding a particular activity, e.g., a determined likelihood that a user of a device is currently walking, and as detailed below, based on a custom assessment of the user of the device, can apply a weight to this value, e.g., making the activity more likely, less likely, or the same likelihood. This changed value can then be evaluated by an activity trigger component 230 of general model components 132 to determine whether the modified likelihood is sufficient to trigger activity output 250. In an example, activity output 250 can cause actions to be performed associated with walking, e.g., step detection, turning on location determining sensors, and other activities associated with walking.

In one or more embodiments, the weighting of output from estimators 215A-D can also be termed as tuning, calibrating, adjusting, boosting, and other similar terms. As noted above, estimators can generate output (e.g., likelihoods of an activity occurring), and as described herein, this output can also be termed estimators parameters. As used herein, weights can be termed personal weights, individual weights, estimator weights, and other similar terms. The terms described in this paragraph are only examples of equivalent terms, and other terms used herein can have equivalent or similar meanings without being specifically noted.

It should also be noted that, as used in multiple example embodiments described herein the nonlimiting example model used by estimators can be a gradient boosting machine (GBM), e.g., a machine learning (ML) approach. One having skill in the relevant art(s), given the description herein, would understand the methodology behind the training of standard estimators, e.g., GBM ML models. As discussed further herein, in one or more embodiments, data collected using sensors 170 can be used to determine weights ($W_{JP}$) applied to alter results the GBM. Notwithstanding the discussion of GBM models herein, one having skill in the relevant art(s), given the description herein would appreciate that other models can also be calibrated based on one or more embodiments.

In one or more embodiments, to address some of the circumstances noted above, personal weight determiner 175 can receive sensor 170 data and select weights 225A-C to modify the output values of general model components 132, including estimators 215A-215D. In this approach, one or more embodiments can use a transfer learning based approach where a standard model has already trained on an available data set and provided on device 105, and once a user has the device, changes can be made to the standard results based on a smaller, individualized data set. To generate this data set, one or more embodiments can do one or more of, collecting data from everyday, normal use (e.g., walking is done frequently), or specifically prompt a user to perform a specific activity, at a specific time, e.g., sitting, running, driving, and other activities.

In one or more embodiments, once one or more estimators 215A-D generate likelihoods of the occurrence of different activities, in accordance with general model components 132, activity trigger component 230 can evaluate the one or more likelihoods of the activities identified by estimators 215A-D and determine whether to trigger the occurrence of events associated with one or more activities, e.g., an activity output 250. Stated differently, activity trigger component 230 can evaluate multiple estimators 215A-D by using ensemble algorithms like Random Forests. In this algorithm, the average of the outputs of relevant estimators is determined, e.g., models in the ensemble. Once the outputs are aggregated, a determination of a triggered activity can be made by activity trigger component 230. Considered within this context, weighting of estimator 215A-D outputs by one or more embodiments can be termed boosting ensemble methods.

Returning to the example, for an example person moving quickly, both walking estimator 215A and running estimator 215B, can generate likelihoods that respective activities are occurring. In a simple determination, activity trigger component 230 can select the highest likelihood and compare this value to a threshold to determine a walking or running activity. In other approaches combinations of other sensors 170 can also provide relevant data, e.g., an accelerometer could determine the vigorousness which an individual is moving.

In one or more embodiments, personal weight applier 134 can apply weights to individual estimator outputs before these estimates are evaluated by activity trigger component 230. Thus, in an example where a model determines that a likelihood of running is 25% and a likelihood of walking is 70%, for a person (e.g., a child or disabled person) determined (by analysis of sensor data by personal weighting determiner 175) to be subject to false running negative results (e.g., the 25% value is erroneously assigned), personal weight determiner 175 can apply a weight 225B that identifies the running estimator 215B as likely having a falsely low value, and personal weight applier 134 can apply weight 225B and increase the likelihood of running being determined from 25% to 75%, thereby beneficially adjusting the application of general model components 132.

It is important to note that, in one or more embodiments using this approach, estimators 215A-D are not modified, this being beneficial because, in some circumstances, the estimators 215A-D could not be altered on device 105. With this approach, in some circumstances, one or more embodiments can improve the accuracy of the system for a specific user of device 105, without having to change the installed models. In an additional benefit of not modifying estimators 215A-D, the retraining of aspects of a standard model in device 105 can require significant computing resources and time, e.g., potentially more resources than device 105, potentially being a smartwatch, has available.

In yet another benefit of the one or more approaches described herein, in some circumstances, the retraining of a standard device model may be impracticable because only a limited data set is available for retraining. For example, a GBM can be trained on data based on 'running' and 'walking' activities available from many users. However, this data set may not represent every kind of human behavior in real life. This may result in decrease in the accuracy of activity recognition.

Turning now to additional detail regarding sensors 170, these component can include, but are not limited to:

Piezoelectric bender elements
Piezoelectric film
Accelerometers (e.g., linear variable differential transformer (LVDT), Potentiometric, Variable Reluctance, Piezoelectric, Piezoresistive, Capacitive, Servo (Force Balance), MEMS)
Displacement sensors
Velocity sensors
Vibration sensors
Gyroscopes
Proximity Sensors
Electric microphones
Hydrophones
Condenser microphones
Electret condenser microphones
Dynamic microphones
Ribbon microphones
Carbon microphones
Piezoelectric microphones
Fiber optic microphones
Laser microphones
Liquid microphones
MEMS microphones The analysis of data from sensor 170 can be performed by different system components, including personal weight determiner 175, using a variety of functions, including, but not limited to:

Average
Standard Deviation
Standard deviation (normalized by overall amplitude)
Variance
Skewness
Kurtosis
Sum
Absolute sum
Root Mean Square (RMS)
Crest Factor
Dispersion
Entropy
Power sum
Centroid (Center of mass)
Coefficient of variation
Zero-crossings Personal weight determiner 175 can also use other approaches to determine weights, including but not limited to, basic heuristics, decision trees, Support Vector Machine, Random Forest, Naive Bayes, elastic matching, dynamic time warping, template matching, k-means clustering, K-nearest neighbors algorithm, neural network, Multilayer perceptron, multinomial logistic regression, gaussian mixture models, and AdaBoost.

FIG. 3 depicts example formulas 300 that can describe the modifying of GBM model parameters, in accordance with one or more embodiments. Repetitive description of like elements employed in other embodiments described herein is omitted for sake of brevity.

FIG. 4 depicts example formulas 400 that can describe using loss functions to select a weight 225A to be applied to an estimator 215A, in accordance with one or more embodiments. Repetitive description of like elements employed in other embodiments described herein is omitted for sake of brevity.

Figure 5:
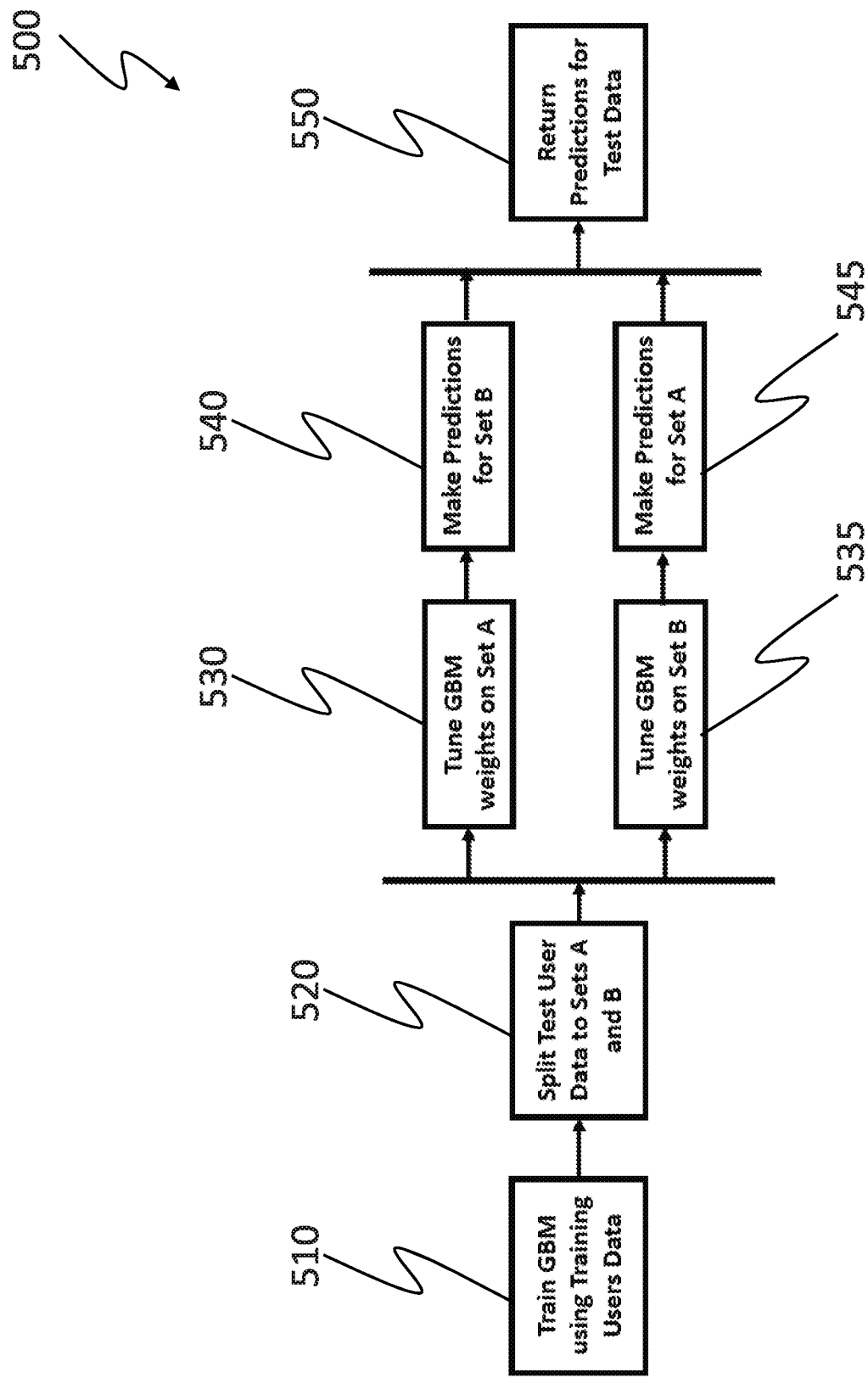
FIG. 5 depicts a flowchart of the one-user-out cross validation (CV) procedure for tuning the GBM model weights and model evaluation, in accordance with one or more embodiments.

FIG. 5 depicts a flowchart 500 of the one-user-out cross validation (CV) procedure for tuning the GBM model weights and model evaluation, in accordance with one or more embodiments. Repetitive description of like elements employed in other embodiments described herein is omitted for sake of brevity.

In this section, flowchart 500 is discussed using two publicly available data sets. The first data set is called "Daily and Sports Activities Data Set," and the second data set is called "PAMAP2 Data-set: Physical Activity Monitoring." In one or more embodiments, one-user-out cross-validation (CV) and F-1 scores can be compared using these data sets for a baseline GBM and a tuned GBM. Flowchart 500 shows the flowchart of the one-user-out CV procedure for tuning the GBM weights and model evaluation, with the baseline GBM one-user-out CV being calculated by training GBM using (N-1) training users data at block 510. At block 520, for tuning the GBM weights, the $N^{th}$ user's data is split to Sets A and B. Initially, at block 530, GBM weights are tuned on Set A and then, at block 540, the tuned GBM is used, at block 550, to make predictions for Set B and vice versa, with blocks 535 and 545. By using this approach, one or more embodiments can use a tuned GBM to calculate one-user-out CV, with a part of the tuning data being used as a validation set to choose the final model based on validation set accuracy.

Figure 6:
FIG. 6 includes a table that provides example features that can be used for activity classification, in accordance with one or more embodiments. To illustrate different concepts, a Daily and Sports Activities Data-Set is discussed below in conjunction with FIGS. 6 and 7.

FIG. 6 includes a table 600 that provides example features that can be used for activity classification, in accordance with one or more embodiments. To illustrate different concepts, a Daily and Sports Activities Data-Set is discussed below in conjunction with FIGS. 6 and 7. Repetitive description of like elements employed in other embodiments described herein is omitted for sake of brevity.

An example Daily and Sports Activities Data-Set has 19 different activities performed by 8 different subjects. The data is collected using accelerometer, gyroscopes, and magnetometers attached at different parts of body of the subjects.

Figure 7:
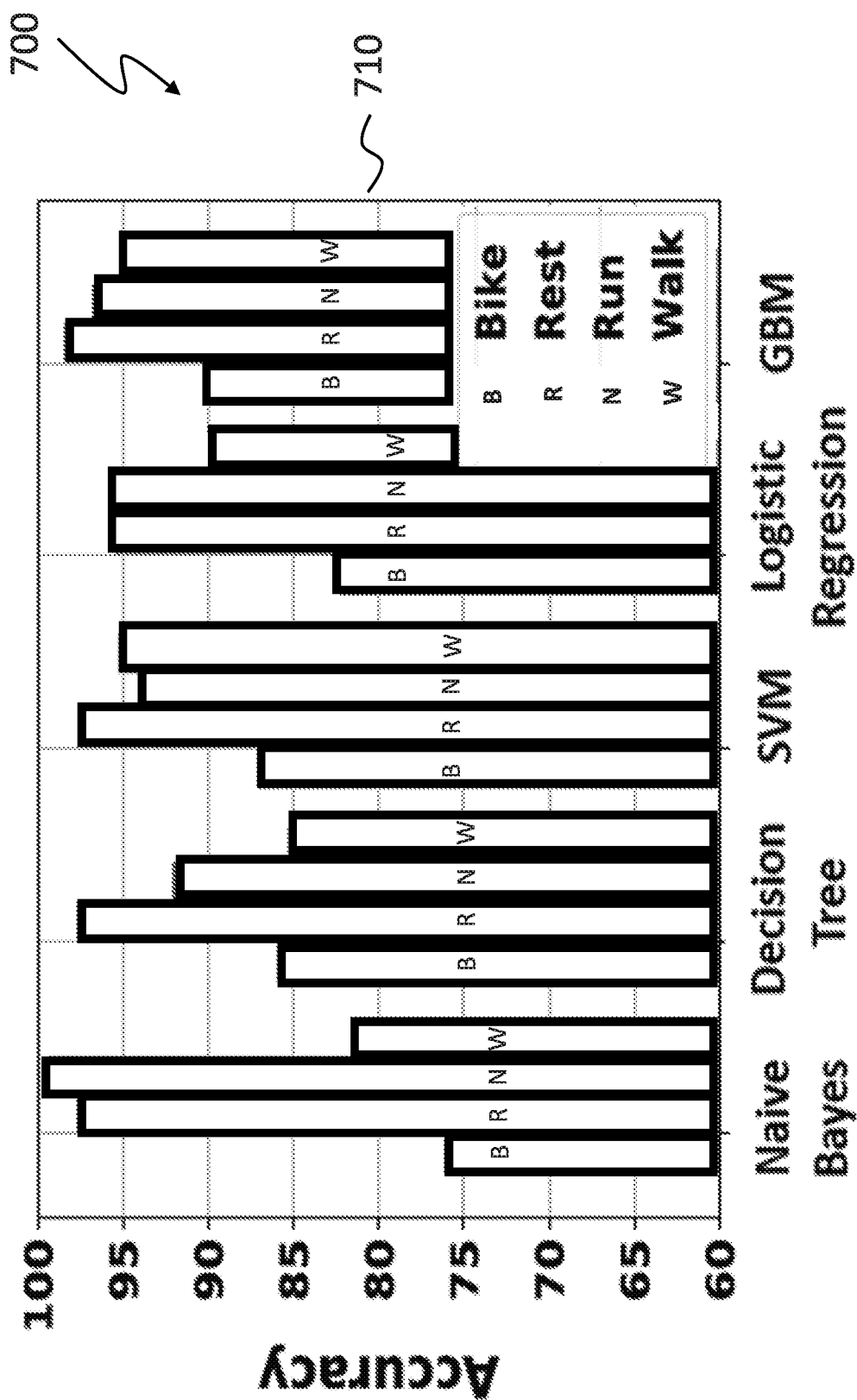
FIG. 7 depicts a comparison between a baseline of a GBM model having one-user-out CV accuracy with other ML models, in accordance with one or more embodiments.

FIG. 7 depicts a comparison 700 between a baseline of a GBM model having one-user-out CV accuracy with other ML models, in accordance with one or more embodiments. Repetitive description of like elements employed in other embodiments described herein is omitted for sake of brevity.

To illustrate aspects of different embodiments discussed herein, data of an accelerometer sensor 170 attached to an arm/wrist are shown in chart 710 for four different activities from this data set: Running, Biking, Resting and Walking. In this example, the data was collected at 25 Hz of sampling frequency, with one second of latency, e.g., a total of 25 samples, collected every second, are used to generate one instance of features in chart 710. FIG. 6 shows different features 600 that were computed using these samples. These features were calculated using accelerometer data about X, Y, and Z axes.

Initially, in FIG. 7, for comparison, the baseline GBM model with one-user-out CV accuracy is depicted as compared with other types of ML models. It should be noted that for 'Rest' and 'Run' classes, every model has high accuracy. However, in this example, the GBM performs better than other models for 'Bike' and 'Walk' classes. In one or more embodiments, these can be handled differently because there is more variety in how users walk and cycle than how users walk and run. One or more embodiments can generate weights based on these types of factors, leading to an increase in accuracy, in some circumstances. This is also due to the reason that different users could walk and do cycling differently than other users.

Figure 8A:
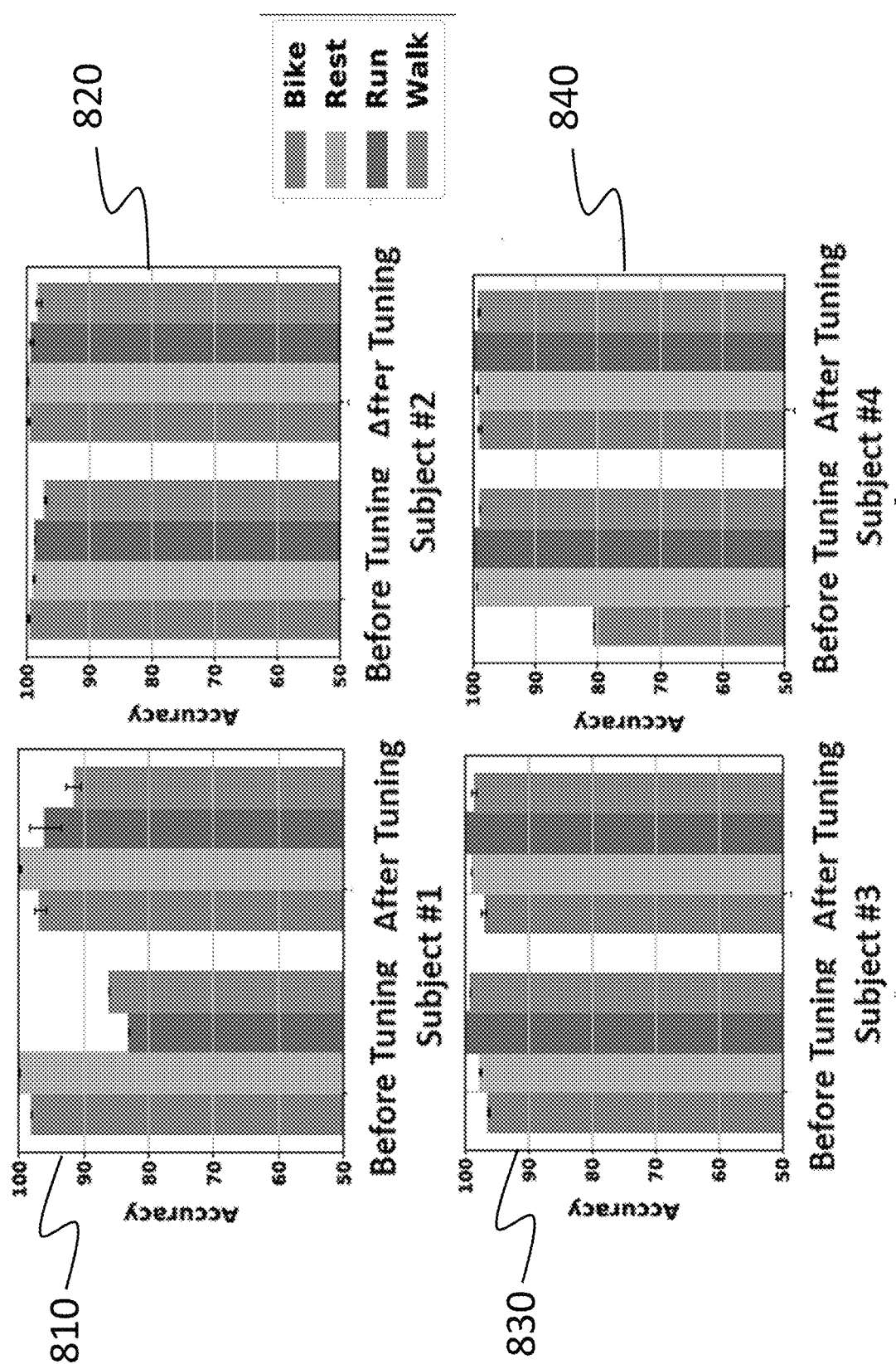
Figure 8B:
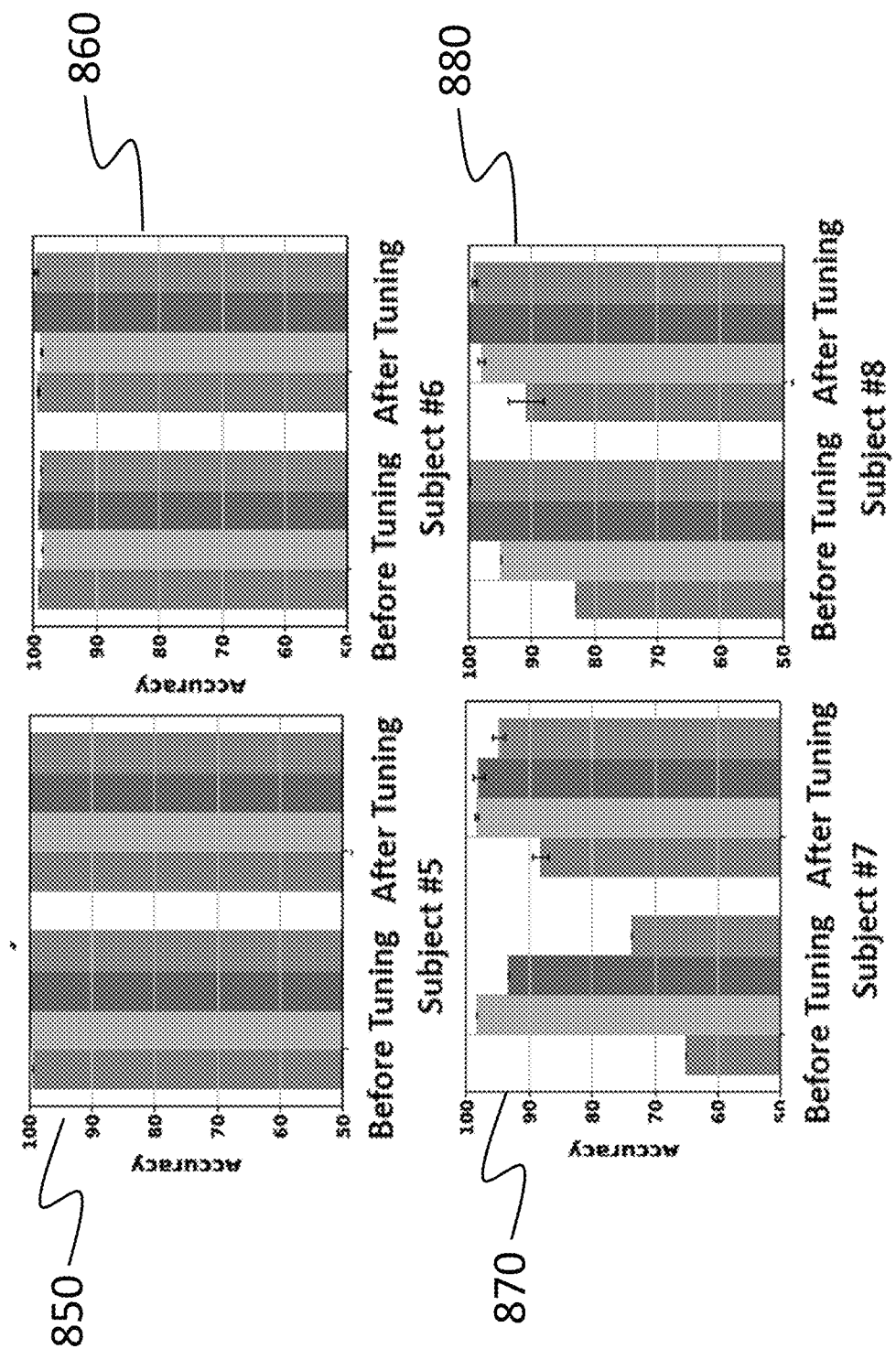

FIGS. 8A-8B, and FIG. 9, continuing this example, respectively depict charts 810-880 and table 900, with accuracy shown before and after the use of generated weights, as described herein. Repetitive description of like elements employed in other embodiments described herein is omitted for sake of brevity.

As depicted in the example data of eight subjects shown in FIGS. 8A-8B, embodiments of the tuning algorithm can be used on the Daily and Sports Activities data set to improve one-user-out CV accuracy. FIGS. 8A-8B, and table 910 in FIG. 9, depict the average increase in the accuracy of each subject before after applications of one or more embodiments described herein. For example, it can be seen that there is some increase in the accuracy of every subject, with a significant increase in the accuracy of 'Bike' and 'Walk' class for subject #7 from 65% and 73% to 88% and 94% respectively. Also, for subject #8, there is an increase of accuracy for the 'Bike' activity from 83% to 90%.

Figure 10:
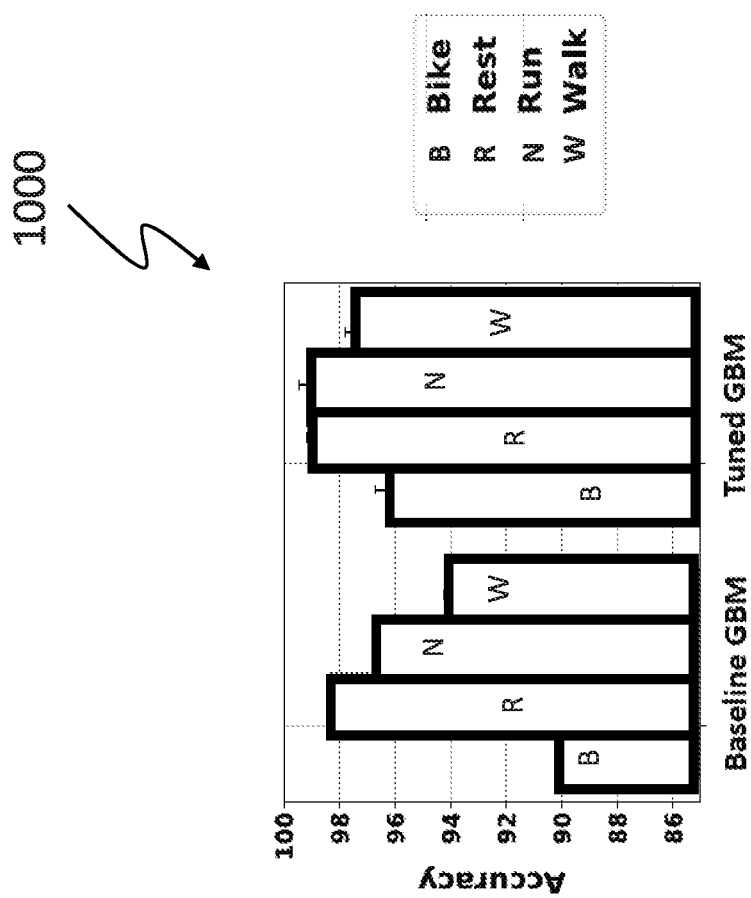
FIG. 10 depicts a chart that shows an average increase in the overall one-user-out CV accuracy for each class after tuning the baseline GBM, in accordance with one or more embodiments.

FIG. 10 depicts a chart 1000 that shows an average increase in the overall one-user-out CV accuracy for each class after tuning the baseline GBM, in accordance with one or more embodiments. Repetitive description of like elements employed in other embodiments described herein is omitted for sake of brevity.

As shown, the example baseline accuracy is 90%, 98%, 96% and 94% for the 'Bike,' 'Rest,' 'Run,' and 'Walk' classes respectively. It should be noted that these accuracy values increase to 96%, 99%, 99%, and 97% respectively, after the one or more of the approaches described herein are applied. Thus, in this example, in some circumstances more than 50% error reduction can be achieved by tuning the GBM on specific user's data, in accordance with one or more embodiments.

Figure 11:
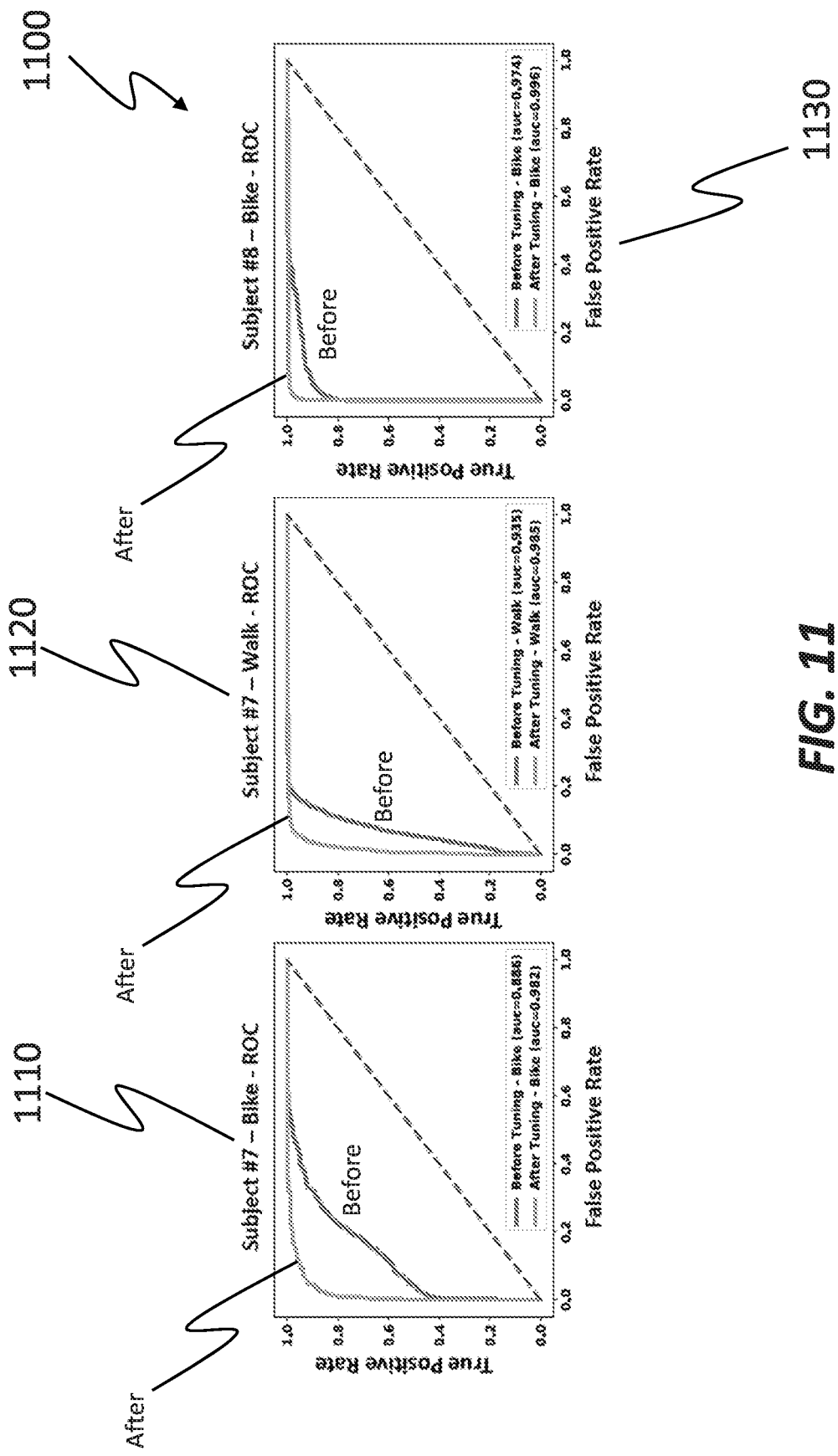
FIG. 11 depicts a chart that depicts a comparison in receiver operating characteristic (ROC) curves for subject #7 and #8 for 'Bike' and 'Walk' classes, to illustrate aspects of one or more embodiments.

FIG. 11 depicts a chart 1100 that depicts a comparison in receiver operating characteristic (ROC) curves (1110, 1120, 1130) for subject #7 and #8 for 'Bike' and 'Walk' classes, to illustrate aspects of one or more embodiments. Repetitive description of like elements employed in other embodiments described herein is omitted for sake of brevity.

As depicted in chart 1110, for the subject #7 'Bike' class, the Area Under Curve (AUC) value increases significantly from 0.886 to 0.982 after tuning, after processing in accordance with one or more embodiments. It should further be noted that, for this data, table 900 of FIG. 9 shows a comparison of the F-1 scores of baseline GBM and GBM tuned in accordance with one or more embodiments, with the overall F-1 score increasing from 0.9456 to 0.9758.

Figure 12:
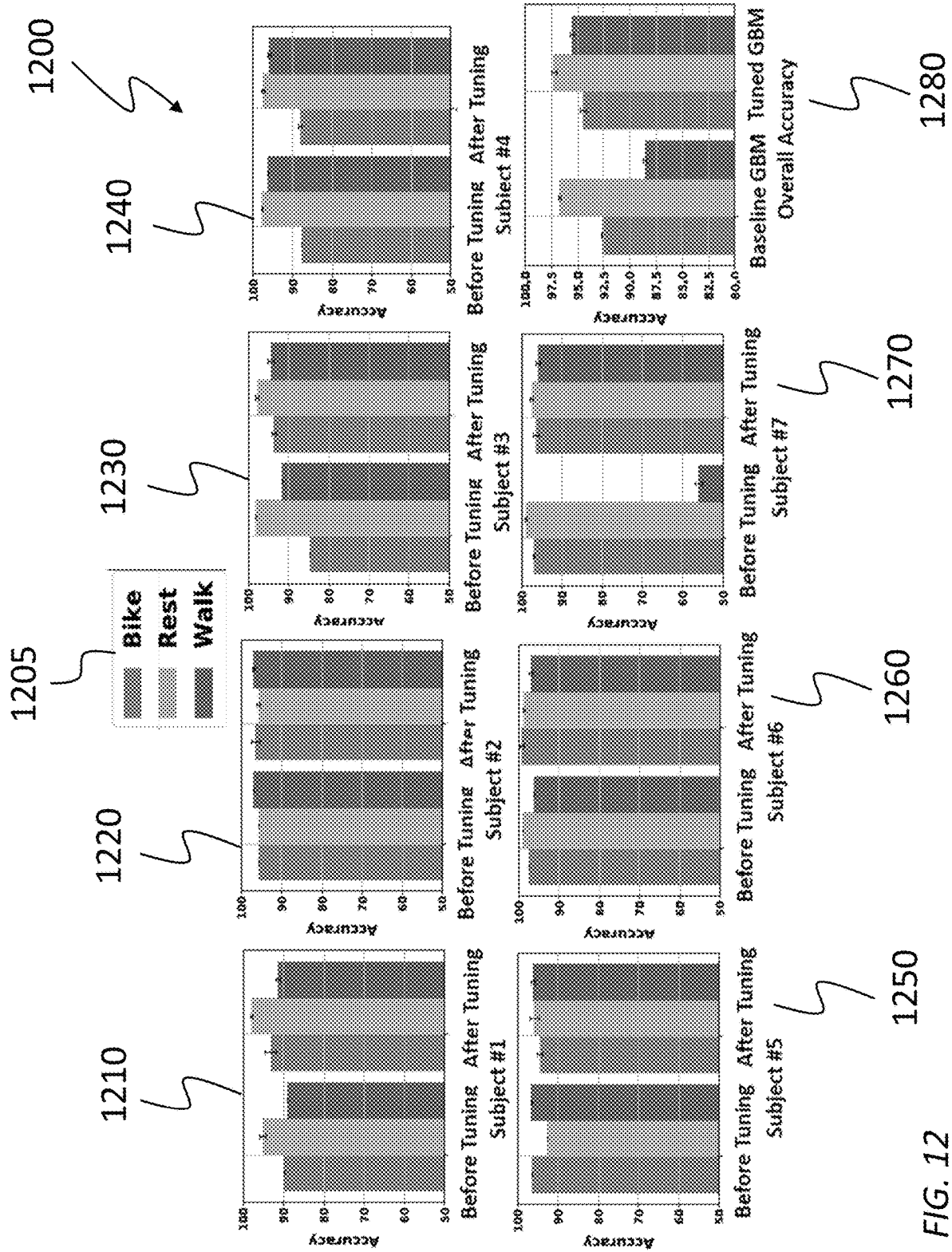

FIGS. 12 and 13, to illustrate additional aspects of one or more embodiments, respectively depict charts 1200 and table 1300 showing illustrative data from another example dataset. Repetitive description of like elements employed in other embodiments described herein is omitted for sake of brevity.

This second example data set, named PAMAP2, is populated with accelerometer data for three different activities (e.g., Biking, Resting, and Walking 1205) performed by nine different subjects. In this example, this data set was collected at 100 Hz, with one second of latency, e.g., data for 100 samples are shown.

For this second example, a process similar to the process shown in flowchart 500 of FIG. 5 is used for training the baseline GBM to find on-user-out CV accuracy. Charts 1210-1280 of FIG. 12 shows an average increase in the one-user-out CV accuracy of each class of subjects, and an overall increase in the CV accuracy, based on tuning the GBM an accordance with one or more embodiments described herein.

As a further example, FIG. 13 depicts table 1300 with a comparison of F-1 scores for baseline GBM and GBM tuned in accordance with one or more embodiments. It should be noted that there is an overall F-1 score increase from 0.9307 to 0.9619 shown, as well as a significant increase in the subject F-1 score of subject #7, e.g., from 0.8117 to 0.9671.

In an additional illustration of features of one or more embodiments, FIG. 12 further indicates in chart 1270 that 'Walk' accuracy of subject #7 increases from 55% to 95%. FIG. 1200 also shows an overall one-user-out CV increase for each class, with the baseline accuracy for the 'Bike', 'Rest' and 'Walk' classes respectively being 92%, 96% and 88%. Additional benefits of one or more embodiments are illustrated by an respective increase of the accuracy of these classes from the baseline value to 94%, 97% and 95%.

One or more embodiments described above may be implemented in the form of program instructions that can be executed by various computer components, and may be stored on a computer-readable recording medium. The computer-readable recording medium may include program instructions, data files, data structures and the like, separately or in combination. The program instructions stored on the computer-readable recording medium may be specially designed and configured for one or more embodiments, or may also be known and available to those skilled in the computer software field. Examples of the computer-readable recording medium include the following: magnetic media such as hard disks, floppy disks and magnetic tapes; optical media such as compact disk-read only memory (CD-ROM) and digital versatile disks (DVDs); magneto-optical media such as optical disks; and hardware devices such as read-only memory (ROM), random access memory (RAM) and flash memory, which are specially configured to store and execute program instructions. Examples of the program instructions include not only machine language codes created by a compiler or the like, but also high-level language codes that can be executed by a computer using an interpreter or the like. The above hardware devices may be changed to one or more software modules to perform the operations of one or more embodiments, and vice versa.

Although one or more embodiments have been described above in connection with specific limitations such as detailed components as well as limited embodiments and drawings, these are merely provided to aid general understanding of the invention. The one or more embodiment described herein are not limited to the above embodiments, and those skilled in the art will appreciate that various changes and modifications are possible from the above description.

Therefore, the spirit of one or more embodiments shall not be limited to the embodiments described above, and the entire scope of the appended claims and their equivalents will fall within the scope and spirit of the invention.

What is claimed is:

1. A method for calibrating a user activity model used by a mobile device, the method comprising:
   receiving sensor data from a sensor of the mobile device, wherein the sensor is operable to detect a plurality of different activities of a user of the mobile device;
   from the sensor, collecting user-specific training data for a specific user of the mobile device performing the plurality of different activities;
   generating a weight for each of the different activities based on the user-specific training data;
   for the specific user, inputting the sensor data into a general model of the mobile device that outputs a likelihood result for each of the plurality of different activities, wherein the general model was trained based on sensor data from a plurality of different users performing the plurality of different activities;
   for the specific user, applying each weight for each of its corresponding one of the different activities to adjust its corresponding likelihood result without modifying the general model and without retraining the general model;
   determining a first one of the different activities is being performed by the specific user by selecting a highest value of the adjusted likelihood results; and
   performing an action on the device for the specific user based on a determination of the first activity, wherein the different activities comprise walking, running, biking, and resting activities, wherein the action comprises turning on step detection and/or location detection for the mobile device if the first activity comprises walking, running or biking, wherein the action comprises turning off the step detection and/or location detection if the first activity is a resting activity.

2. The method of claim 1, further comprising:
   facilitating an assessment of physical characteristics of the specific user of the mobile device, wherein the physical characteristics comprise age and whether the user is disabled, and wherein generating each weight is based on the assessment of the physical characteristics of the specific user.

3. The method of claim 2, wherein each weight is generated to improve, for the specific user of the mobile device, an accuracy of each corresponding modified likelihood result.

4. The method of claim 2, wherein the general model is implemented on the mobile device.

5. The method of claim 1, wherein the determining the first activity comprises comparing the likelihood results of the plurality of different activities.

6. The method of claim 1, wherein the applying the weight to each likelihood result comprises increasing or decreasing such likelihood result.

7. The method of claim 1, wherein the receiving the sensor data comprises, receiving data from at least one of, an accelerometer, a magnetometer, or a gyroscope.

8. A mobile device, comprising:
a sensor;
a processor; and
a memory that stores executable instructions that, when executed by the processor, facilitate performance of operations, comprising:
receiving sensor data from the sensor, wherein the sensor is operable to detect a plurality of different activities of a user of the mobile device;
from the sensor, collecting user-specific training data for a specific user of the mobile device performing the plurality of different activities;
generating a weight for each of the different activities based on the user-specific training data;
for the specific user, inputting the sensor data into a general model that outputs a likelihood result for each of the plurality of different activities, wherein the general model was trained based on sensor data from a plurality of different users performing the plurality of different activities;
for the specific user, applying each weight for each of its corresponding one of the different activities to adjust its corresponding likelihood result without modifying the general model and without retraining the general model;
determining a first one of the different activities is being performed by the specific user by selecting a highest value of the adjusted likelihood results; and
performing an action on the device for the specific user based on a determination of the first activity, wherein the different activities comprise walking, running, biking, and resting activities, wherein the action comprises turning on step detection and/or location detection for the mobile device if the first activity comprises walking, running or biking, wherein the action comprises turning off the step detection and/or location detection if the first activity is a resting activity.

9. The mobile device of claim 8, the operations further comprising:
facilitating an assessment of physical characteristics of the specific user of the mobile device, wherein the physical characteristics comprise age and whether the user is disabled, and wherein generating each weight is based on the assessment of the physical characteristics of the specific user.

10. The mobile device of claim 9, wherein each weight is generated to improve, for the specific user of the mobile device, an accuracy of each corresponding modified likelihood result.

11. The mobile device of claim 9, wherein the general model is implemented on the mobile device.

12. The mobile device of claim 8, wherein the determining the first activity comprises comparing the likelihood results of the plurality of different activities.

13. The mobile device of claim 8, wherein the applying the weight to each likelihood result comprises increasing or decreasing such likelihood result.

14. The mobile device of claim 8, wherein the sensor comprises one or more of:
an accelerometer,
a magnetometer, or
a gyroscope.

15. A computer-readable recording medium having program instructions that can be executed by various computer components to perform operations comprising:
receiving sensor data from a sensor of a mobile device, wherein the sensor is operable to detect a plurality of different activities of a user of the mobile device;
from the sensor, collecting user-specific training data for a specific user of the mobile device performing the plurality of different activities;
generating a weight for each of the different activities based on the user-specific training data;
for the specific user, inputting the sensor data into a general model of the mobile device that outputs a likelihood result for each of the plurality of different activities, wherein the general model was trained based on sensor data from a plurality of different users performing the plurality of different activities;
for the specific user, applying each weight for each of its corresponding one of the different activities to adjust its corresponding likelihood result without modifying the general model and without retraining the general model;
determining a first one of the different activities is being performed by the specific user by selecting a highest value of the adjusted likelihood results; and
performing an action on the device for the specific user based on a determination of the first activity, wherein the different activities comprise walking, running, biking, and resting activities, wherein the action comprises turning on step detection and/or location detection for the mobile device if the first activity comprises walking, running or biking, wherein the action comprises turning off the step detection and/or location detection if the first activity is a resting activity.

16. The computer-readable recording medium of claim 15, wherein the operations further comprise:
facilitating an assessment of physical characteristics of the specific user of the mobile device, wherein the physical characteristics comprise age and whether the user is disabled, and wherein generating each weight is based on the assessment of the physical characteristics of the specific user.

17. The computer-readable recording medium of claim 16, wherein each weight is generated to improve, for the specific user of the mobile device, an accuracy of each corresponding modified likelihood result.

* * * * *